United States Patent [19]

Werner

[11] Patent Number: 4,989,597
[45] Date of Patent: Feb. 5, 1991

[54] APPARATUS FOR ADMINISTRATION OF AT LEAST TWO GASES TO A PATIENT

[76] Inventor: Olof Werner, Lund, Sweden

[21] Appl. No.: 399,512

[22] PCT Filed: Mar. 8, 1988

[86] PCT No.: PCT/SE88/00106
§ 371 Date: Aug. 30, 1989
§ 102(e) Date: Aug. 30, 1989

[87] PCT Pub. No.: WO88/06903
PCT Pub. Date: Sep. 22, 1988

[30] Foreign Application Priority Data

Mar. 9, 1987 [SE] Sweden ................................. 8700977

[51] Int. Cl.$^5$ ..................... A61M 15/00; A61M 16/00
[52] U.S. Cl. ........................... 128/203.12; 128/203.14;
 128/205.11; 128/205.12; 128/204.14;
 128/204.21
[58] Field of Search ....................... 128/203.12, 203.14,
 128/203.25, 204.18, 204.21, 204.22, 204.26,
 205.11, 205.14, 205.12, 205.16, 205.27, 205.13,
 205.29, 204.13, 204.14, 204.15, 204.16, 204.17,
 204.28, 203.28

[56] References Cited

U.S. PATENT DOCUMENTS

| | | | |
|---|---|---|---|
| 3,046,979 | 7/1962 | Andreasen | 128/204.28 |
| 3,814,092 | 6/1974 | Simionesw et al. | 128/204.14 |
| 4,127,121 | 11/1978 | Westenskow et al. | 128/203.14 |
| 4,345,612 | 8/1982 | Koni et al. | 128/203.14 |
| 4,453,543 | 6/1984 | Kohnke et al. | 128/205.12 |
| 4,552,139 | 11/1985 | Altner et al. | 128/204.14 |
| 4,596,246 | 6/1986 | Lyall | 128/205.12 |
| 4,602,653 | 7/1986 | Ruiz-Vela et al. | 128/205.11 |
| 4,651,729 | 3/1987 | Rae | 128/203.14 |
| 4,770,168 | 9/1988 | Rusz et al. | 128/203.14 |

Primary Examiner—Eugene H. Eickholt
Attorney, Agent, or Firm—Brooks & Kushman

[57] ABSTRACT

An apparatus for administration of at least two gases to a patient is described. The apparatus comprises a patient circuit (40) which consists of a circle system for rebreathing and a drive circuit (20), and which is provided with delivery means (45, 46) for supplying fresh gas, and a carbon dioxide absorber (44), the apparatus further comprising an actual value transducer (47) for the gas concentration of one gas type, a desired value transducer (81) for indicating the desired gas concentration, and a control device (80) for maintaining said gas concentration. The apparatus is characterised in that the patient circuit and the drive circuit communicate with each other via a gas switching unit or exchanger (30) for open separation, and that the control device (80) comprise a calculating means for determining the gas volume and gas type to be supplied to the patient circuit (40) so as to obtain the desired value concentration.

30 Claims, 7 Drawing Sheets

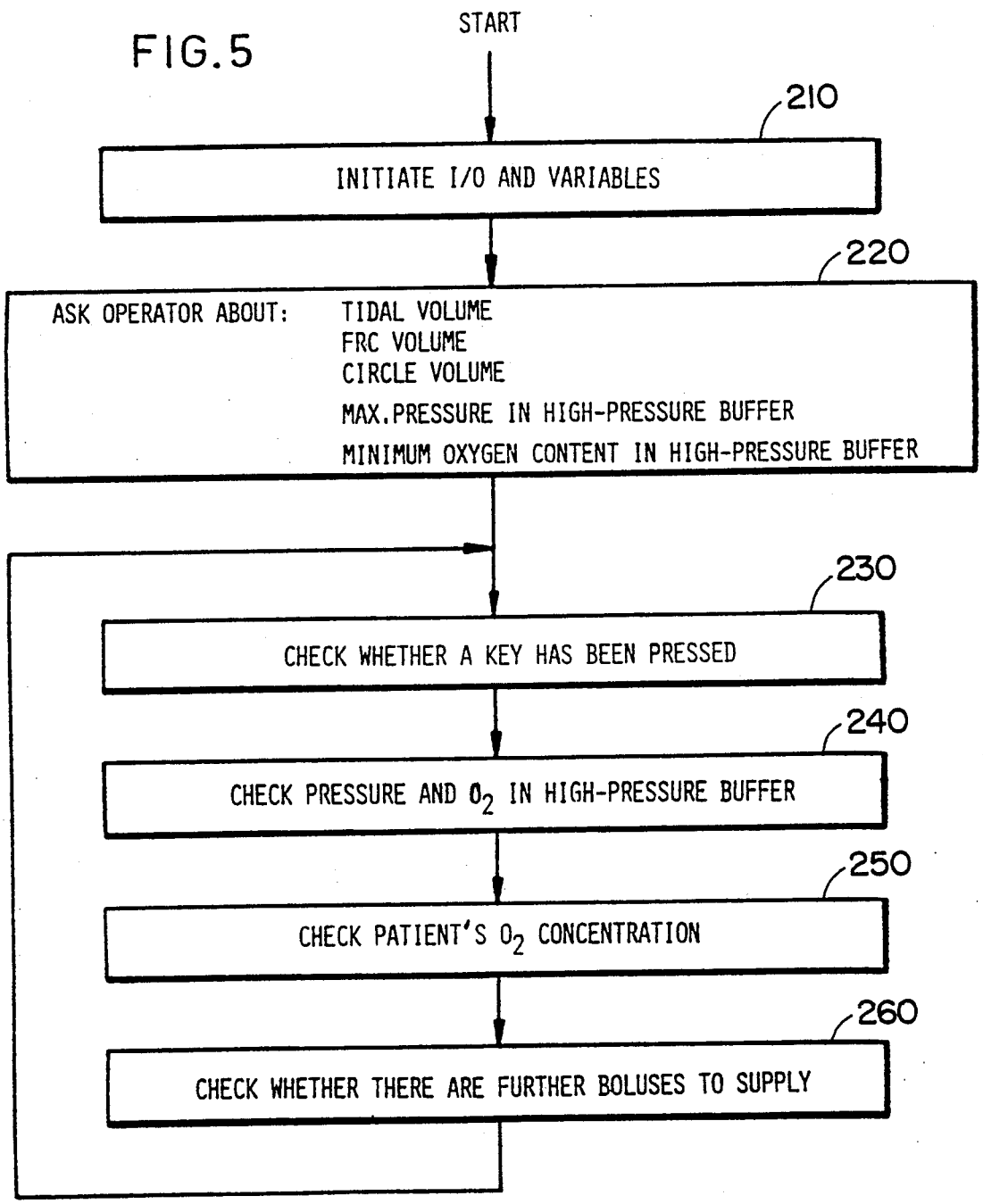

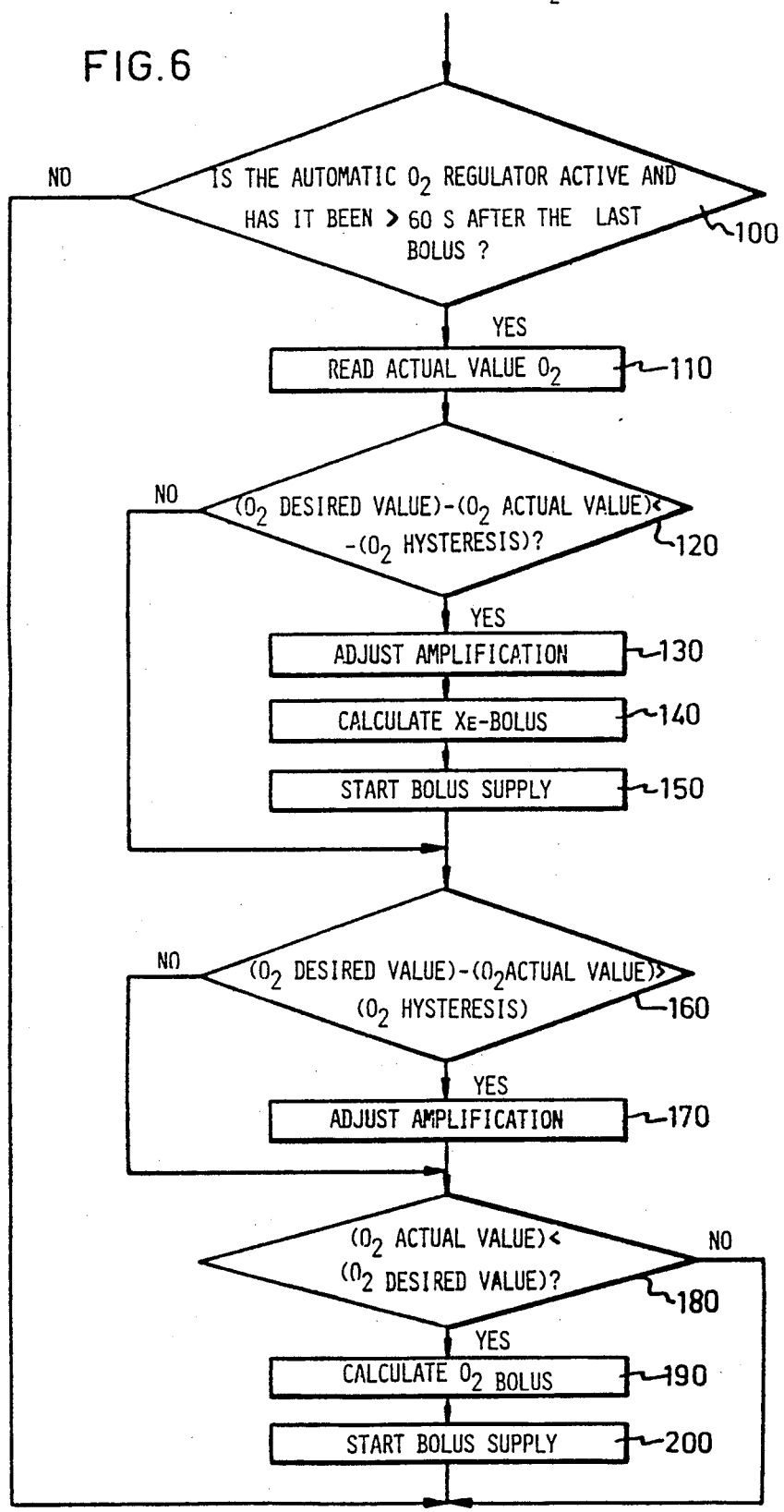

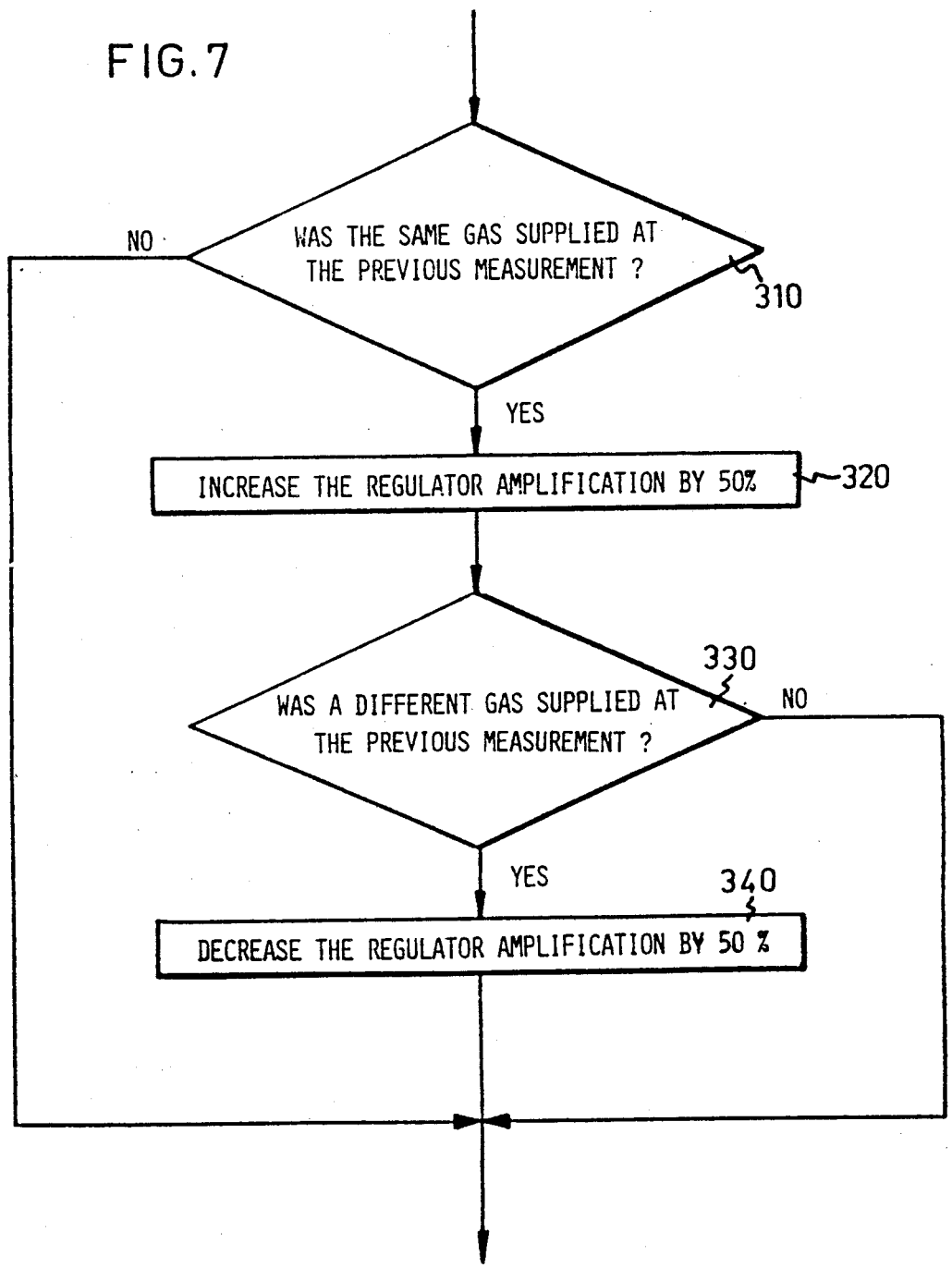

APPARATUS FOR ADMINISTRATION OF AT LEAST TWO GASES TO A PATIENT

The invention relates to an apparatus for administration of at least two gases to a patient, according to the preamble of claim 1.

Such an apparatus for anaesthetic purposes is disclosed in U.S. Pat. specification No. 4,127,121. The circle system with the absorber provides for rebreathing and thus brings the advantage that expensive gases are saved and the loss of moisture and heat is minimised. Moreover, environmental hygiene aspects necessitate keeping down the consumption of anaesthetic gases. The expiration gas is supplied to a bellows which forms part of the drive circuit and presses the gases back to the patient's lungs via the carbon dioxide absorber. The patient circuit and the drive circuit form a closed system.

According to the above-mentioned patent specification, both the concentration of one gas type and the volume variation in the system must be measured so that a desired gas mixture with a minimum consumption of anaesthetic gases can be maintained. It appears from this patent specification that the fresh gas is supplied continuously, which implies that considerable amounts of excess gas must be exhausted from the patient circuit via a valve (not shown).

Rebreathing is essential, when expensive gases are administered, such as anaesthetic gases, helium which is used for treating severe cases of asthma, xenon which is used as contrast medium in computer tomography and as anaesthetic gas, etc. At the same time, respirator ventilation under anaesthetic can be highly advantageous in that, on the one hand, the anaesthetist and/or the nurse is free to perform other important duties and, on the other hand, the respirator is a better means than manual ventilation for establishing an optimal patient breathing pattern. In the treatment of asthma, the respirator can be of vital importance.

One prior art closed system is shown in FIG. 1a. FIG. 1a shows a closed system with an anesthetic bag 1 in communication with an excess valve 2. The excess valve 2, in turn, is in communication with a CO2 absorber which is in communication with a vaporizer 4. The vaporizer 4 supplies fresh gas to a patient 5. Elements common to FIGS. 1a, 1b and 1c have the same reference numeral.

One possibility of combining the respirator circuit and the anaesthetic circuit is illustrated in FIG. 1b wherein a respirator 6 is made to drive a bellows 7 which is enclosed in a container 8 and operates the anaesthetic circuit. This is the so-called bag-in-bottle principle which can also be built into the respirator 6 proper. However, the bag-in-bottle principle comprises some special arrangements; on the one hand there is the arrangement which has given the method its name and, on the other hand, the function of the excess valve 2 must be checked.

A further possibility of combining the respirator circuit (drive circuit) and the patient circuit (receiver a circuit) is to connect between them a switching unit 9 or exchanger which openly separates the gases in the two circuits as illustrated in FIG. 1e. During inhalation, the gas of the respirator 6 (e.g. oxygen) is supplied to the exchanger. The pressure is propagated to the patient circuit for operation thereof. During expiration, the gas flows back. In its simplest form, the exchanger may be an empty container. The best way is, however, to design the exchanger such that the front therein, between respirator gas and patient gas, becomes as well defined as possible. This can be achieved by giving the exchange the form of a tube.

An apparatus for inhalation anaesthesia comprising a gas exchanger between the drive circuit and the patient circuit is described in the paper "A new generation of anaesthetic ventilators" by A. P. Adams and J. D. Henville in Anaesthesia 1977, Vol. 32, pp. 34-40. The described exchanger is in the form of a corrugated tube, and serves to avoid dilution of anaesthetic gas. The fresh gases for anaesthetic and inhalation are supplied continuously and controlled by a flow meter.

The object of the invention is to control in a simple manner the gas concentration in the patient circuit with a minimum supply of fresh gas, thereby to improve the saving of e.g. expensive anaesthetic gas. The object is achieved by means of a communication, stated in the characterising clause of claim 1, between the patient circuit and the drive circuit via a or exchanger, and a control device calculating and supplying fresh gas volumes to the circle in response to the desired value and actual value concentrations of a gas in the patient circuit.

The invention is based on the surprising discovery that a system with open separation between the patient and drive circuits obtains an inherent equilibrium so that the gas concentration in the patient circuit is more readily controllable by the supply of small amounts of one or the other gas type, depending on whether the gas concentration is too low or too high. Only this insight renders it possible to minimise the consumption of expensive anaesthetic gas, such as xenon, without measuring the volume variations in the patient circuit.

This important simplification makes it possible to effectively control, by electronic means, the gas concentration in the patient circuit and facilitates the anaesthetist's work, particularly during long anaesthesia, while simultaneously providing a highly reliable system ensuring the patient's safety.

The invention thus allows a very small supply of fresh gas, while maintaining full safety for the patient. If, for some reason, the supply of fresh gas to the patient circuit should be too low, a given amount of oxygen is administered automatically to the patient via the exchanger from the drive circuit. Further, because of the small supply of fresh gas, the invention also causes the amount of anaesthetic gas escaping from the patient circuit restricted to the small amount which passes via the exchanger into the drive circuit and thus is effectively recovered.

Further advantages obtained by using the exchanger are, inter alia, that the connection between the respirator circuit and the patient circuit becomes simple and at the same time inexpensive, and that the excess gas from the patient circuit is recovered via the respirator. Moreover, exchanger functions as a buffer for volume variation in the patient's lungs.

It is also easier than before to use a so-called closed system. If the flow of fresh gas is shut off, a net flow towards the patient occurs through the exchanger owing to the patient's oxygen consumption. The fresh gas is then automatically replaced by oxygen which flows from the respirator part. In a conventional closed system, the fresh gas flow must continuously be balanced in relation to the oxygen content and volume in the patient circuit.

The invention will now be described in detail below, reference being had to the drawing in which:

FIGS. 5–7 illustrate a flow chart for data control of the fresh gas supply.

Figure 1A:
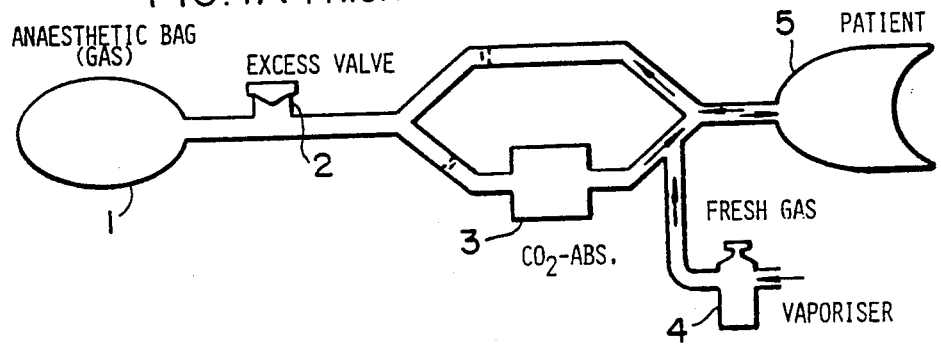
FIG. 1A illustrates a prior art closed circle system with an anaesthetic gas bag.
Figure 1B:
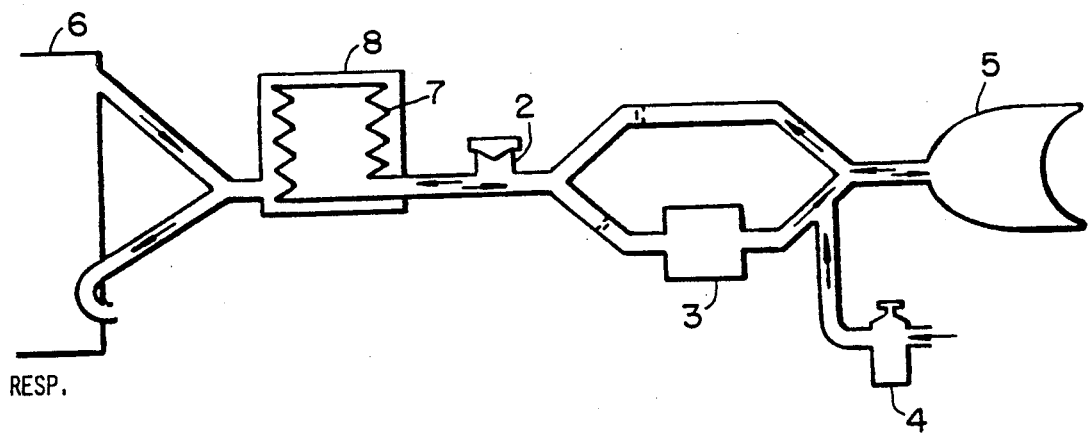
FIG. 1B shows the same system in a "bag-in-bottle" variant and a respirator as the drive circuit.
Figure 1C:
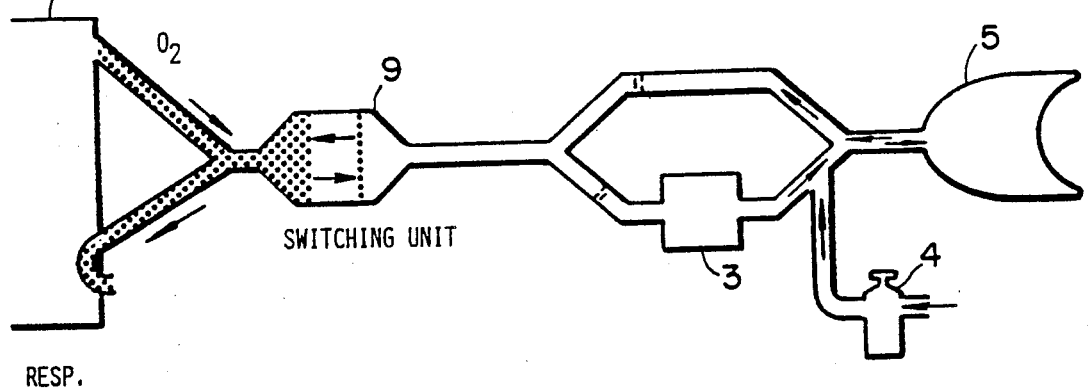
FIG. 1C shows the circle system with a switching unit or exchanger for open separation, and the respirator as the drive circuit.
Figure 2:
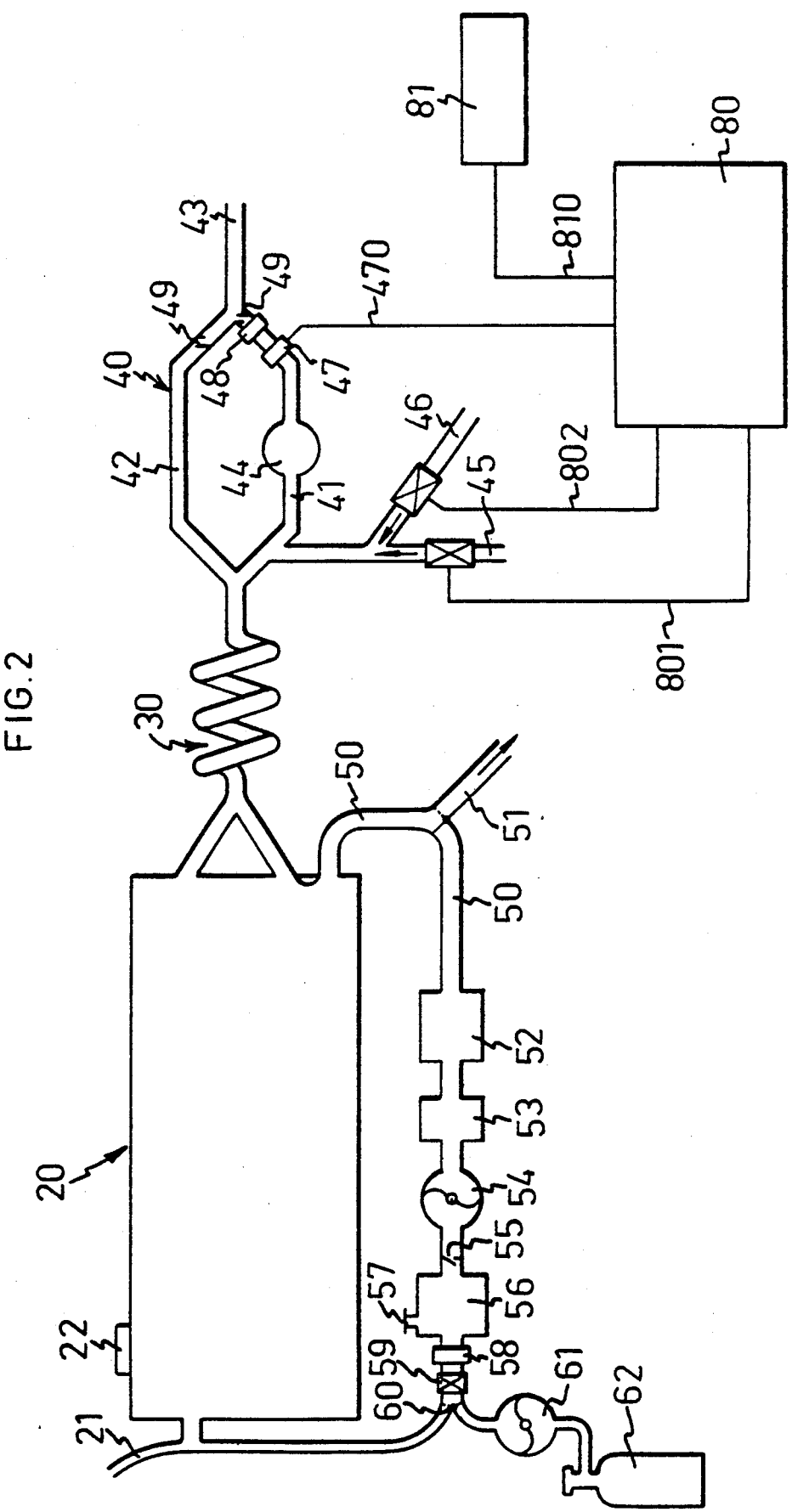
FIG. 2 illustrates a first embodiment of the inventive apparatus for inhalation anaesthesia.

According to the embodiment shown in FIG. 2, the apparatus is divided into two parts, i.e. the drive circuit 20 and the patient circuit 40. The two circuits communicate with each other via the exchanger 30 which is a tube having an internal volume of 2–3 liters. The exchanger prevents mixing of the gases in the two circuits. The drive circuit 20 contains at least 85% $O_2$, and the remainder is anaesthetic gas, such as xenon, which is gradually accumulated. The drive circuit 20 consists of e.g. a Siemens-Elema Ventilator 900. The drive circuit further comprises a conduit 21 for supplying oxygen when necessary, and an oxygen meter 22. The drive circuit is also provided with a return flow conduit 50 which comprises a two-way valve 51 between the atmosphere and the drive circuit. The two-way valve 51 is open to the atmosphere until the anaesthetic gas supply is started. The two-way valve 51 is followed by a water absorber 52 for eliminating technical difficulties caused by moisture. An additional absorber 53 may be arranged, if required, to prevent chemical attack on the equipment. The absorber 53 absorbs gases which are aggressive towards metal and plastics in the apparatus, for example halothane and/or isoflurane. A compressor 54 is arranged to increase the pressure from 0 to about 1–7 atm. gauge, and is followed first by an intermediate nonreturn valve 55, and then by a high-pressure buffer 56. The high-pressure buffer 56 absorbs volume increases in the entire system. Such increases can occur, when a sudden change of the gas content in the patient circuit is required. However, the buffer usually operates at its lower limit of 1 atm. gauge, since more oxygen is consumed than supplied via a valve 46. The high-pressure buffer 56 also includes a safety valve 57 which opens at 7 atm. gauge. The high-pressure buffer 56 is followed by an oxygen meter 58 which in turn is followed by an outlet valve 59 adjacent the high-pressure buffer. The outlet valve 59 maintains the buffer pressure at the desired value. A two-way valve 60 between the gas bottle and drive circuit opens to the bottle, when the oxygen content in the drive circuit is lower than a given value (e.g. 85%) and continues to be open until the value has risen to another given value (e.g. 95%). The gas bottle 62 facilitates recovery of the anaesthetic gas. Between the two-way valve 60 and the gas bottle 62, there is a high-pressure compressor 61 for suppling the bottle 62.

The patient circuit 40 comprises an inhalation leg 41, an expiration leg 42 and a patient insert member 43. A carbon dioxide absorber 44 is arranged in the inhalation leg 41 adjacent the exchanger 30. In the proximity of the carbon dioxide absorber 44, there are arranged solenoid valves 45 and 46 for supplying anaesthetic gas and oxygen, respectively. In the proximity of the solenoid valves 45 and 46, there are arranged an oxygen meter 47 which is an actual value transducer for the oxygen concentration, and an oxygen meter 48 for checking purposes. These meters may be included in the patient insert member 43, but may also be arranged at a different point in the patient circuit. Also the solenoid valves 45 and 46 can be alternately positioned and can be connected both in the proximity of and at a distance from the carbon dioxide absorber 44. The inhalation leg 41 and the expiration leg 42 are provided with suitably positioned nonreturn valves 49. It thus appears from the above description that the drive circuit serves four functions, viz.:

(a) it functions as a ventilator and thus operates the lungs,
(b) it is a source of oxygen,
(c) it buffers volume variations in the entire system, and
(d) it accumulates xenon and when the content has reached a given value, the gas mixture is supplied to an accumulator bottle for recovery later on.

Below follows a description of the function of the apparatus which is controlled by a microprocessor 80 receiving input signals from the $O_2$ meter 47 and the desired value transducer 81 via lines 470 and 810, respectively. The output signals from the microprocessor are delivered via lines 801 and 802 of the solenoid valves 45 and 46. First, the circle system comprising the exchanger 30 and the patient circuit 40 is filled with oxygen by a supply of for instance 2–10 liters $O_2$ per minute via the solenoid valve 46. The two-way valve 51 has been set in the atmosphere position. The desired oxygen concentration is set, and at the same time a number of check-ups of the apparatus 10 are carried out by the microprocessor according to the flow chart shown in FIG. 5.

At block 210, of the flowchart level 1, the first function carried out by the microprocessor is to initiate I/O and variables of the system.

At block 220, the operator is interrogated about tidal volume, FRC volume, circle volume, maximum pressure in high-pressure buffer and minimum oxygen content in high-pressure buffer.

At block 230, the microprocessor checks whether a key has been pressed;

At block 240, the microprocessor checks pressure and $O_2$ in the high-pressure buffer.

At block 250, the microprocessor checks the patient's $O_2$ concentration.

Finally, at block 260, the microprocessor checks whether there are further boluses to supply.

Based on the known volume of the circle system and the patient's assumed lung volume as well as the assumed virtual distribution volume of the anaesthetic gas in the patient's body, which together constitute the mixing volume, the microprocessor calculates the amount of anaesthetic gas required to obtain the intended oxygen content. To avoid hypoxia, the calculation is made by a certain margin. The calculated anaesthetic gas volume is infused, and the excess gas is exhausted via the exchanger 30.

After starting up, the gas supply is controlled via the solenoid valves 45 and 46, based on the $O_2$ concentration as read from the meter 47. As shown in FIG. 6, there is also a time control unit in box 100 for controlling the interval in the fresh gas supply. The interval is chosen by the operator when the microprocessor is initiated.

As appears from FIG. 6, the actual value of the oxygen content in the circle system is now determined by the oxygen meter 47. Subsequently, the difference between the desired oxygen concentration and the actual oxygen concentration is calculated in box 120. If this difference is less than the hysteresis of the $O_2$ concentration, xenon is supplied according to boxes 130 to 150 in the following manner: if xenon was supplied at the previous measurement, the regulator amplification increases by 50%. If oxygen was supplied at the previous measurement, the regulator amplification decreases by 50%. The volume to be supplied is calculated according to the equation: absolute value ln (desired $O_2$ concentration/present $O_2$ concentration)×(tidal volume+residual volume+volume of the circle system)×(regulator amplification), where the volume supplied is allowed to be ten times the tidal volume at most. The volume is supplied via the solenoid valve, if the volume is not too small (about 10 ml). If, however, the above difference is greater than the hysteresis of the $O_2$ concentration, $O_2$ is supplied as follows: if oxygen was supplied at the previous measurement, the regulator amplification increases by 50%. If xenon was supplied at the previous measurement, the regulator amplification decreases by 50%. The volume to be supplied is calculated according to the equation above. The oxygen volume is supplied, if the volume is not too small (about 10 ml). The oxygen volume is supplied to the circle system as described in boxes 160 to 200. The description of the adjustment of the regulator amplification is illustrated in FIG. 7, boxes 310 to 340.

In the return flow conduit 50 of the drive circuit, the anaesthetic gas is accumulated, after water has been separated in the absorber 52, and pollution gases in the form of e.g. halothane have been separated in the absorber 53. The pressure of the returning gas is increased in the compressor 54, and this gas is supplied to the accumulator bottle 62 via the high-pressure compressor 61, when the anaesthetic gas content exceeds a given value. Should the pressure at the outlet valve 59 of the high-pressure buffer 56 drop so far that the ventilator function of the drive circuit cannot be maintained, oxygen is supplied via the conduit 21. When the accumulator bottle 62 is full, it can be used for recovering anaesthetic gas in a recovery unit.

Figure 3:
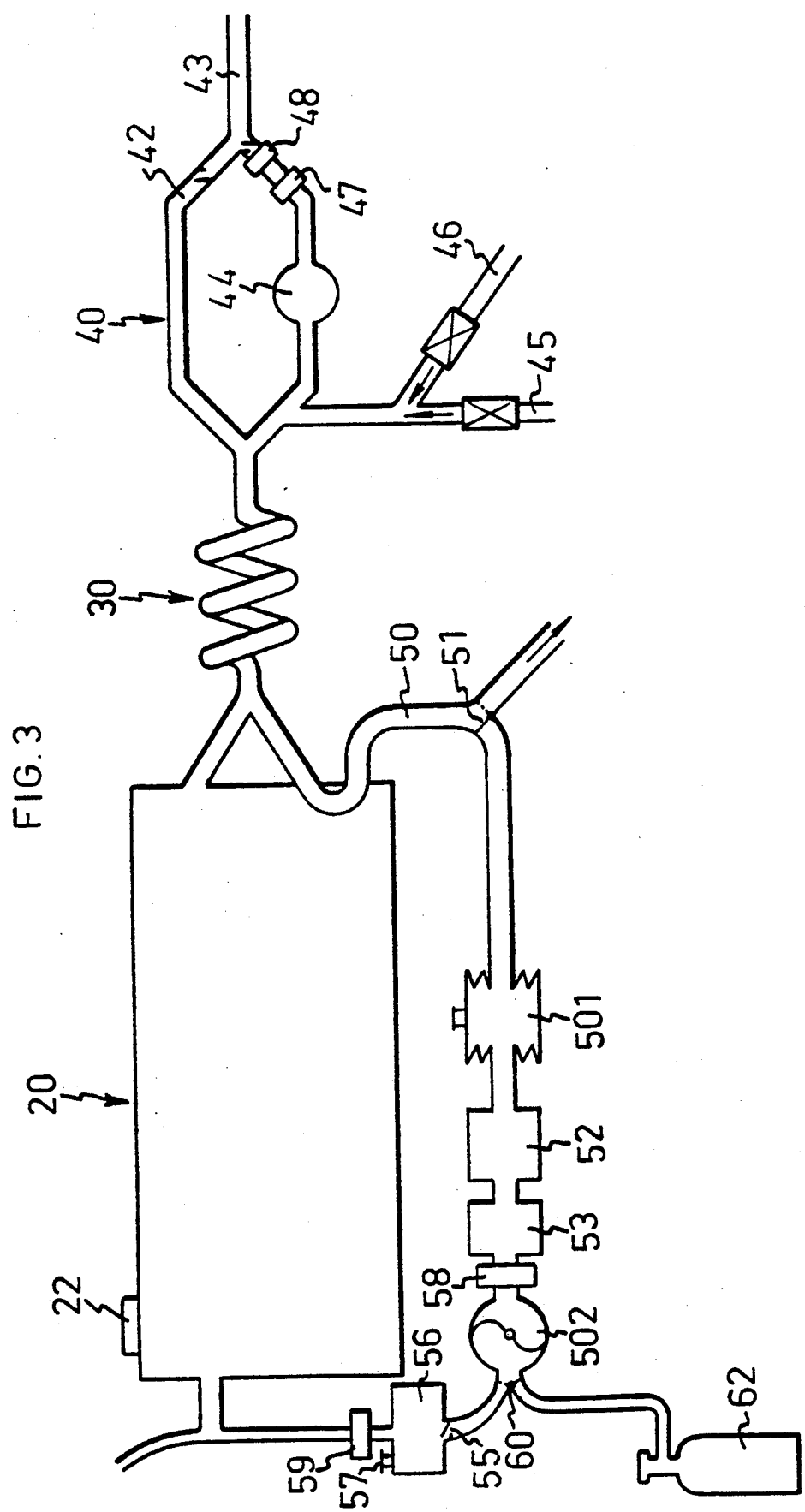
FIG. 3 is the same as FIG. 2, except for the drive circuit conduit for recovery of anaesthetic gas.

FIG. 3 illustrates an alternative embodiment for recovering anaesthetic gas in the return flow conduit 50 of the drive circuit. In this alternative, only one compressor is required, and the compressor 502 supplies both the bottle 62 and the high-pressure buffer 56. This compressor must have a suction effect to propel the gas through the two absorbers 52 and 53. The low-pressure buffer 501 comprises a bellows (about 1-2 liters).

Figure 4:
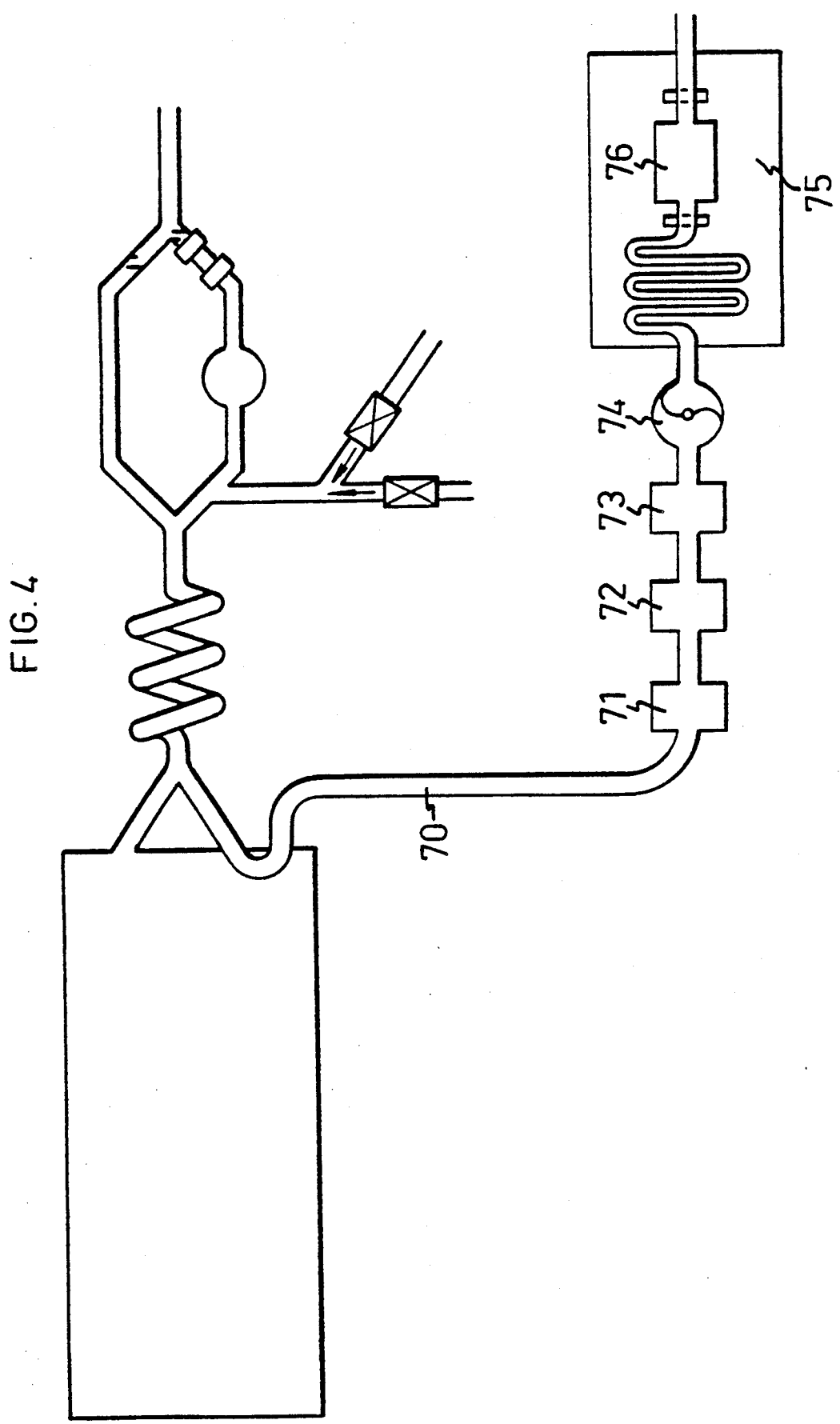
FIG. 4 is also the same as FIG. 2, except for the drive circuit conduit for recovery of anaesthetic gas.

A further alternative for recovering anaesthetic gas is shown in FIG. 4. When the content of the anaesthetic gas (e.g. xenon) is very low, the gas can be processed in a zeolite filter, whereby the temperature is reduced and the pressure rises. The outlet gas from the drive circuit 20 is discharged through the outlet conduit 70 where it is purified of carbon dioxide, water vapour and, possibly, high-molecular gases (isofluran type) in absorbers 71, 72, 73 for the respective substance. The remaining gas, i.e. $O_2$ with an admixture of xenon, is compressed in the compressor 74, cooled in the cooling unit 75 and enters a zeolite filter 76, where the xenon is trapped. Additional oxygen can optionally be supplied at the end of the process to ensure that the gas mixture in the zeolite container consists of xenon-oxygen. Then the filter can be processed for recovering xenon.

The exchanger may be alternatively designed, in its simplest form as a tube. The exchanger may also comprise a plurality of tubes connected in parallel or in series. The exchanger can also be filled with corrugated, folded and/or laminated material or like material, and also be filled with balls or pellets, and can further, or alternatively, be filled with porous material, fibers, metal shavings mesh or the like.

The embodiments shown illustrate the value of the invention for inhalation anaesthesia. In the same advantageous manner, the invention may be used for, inter alia, computer tomography, where xenon is used as a contrast medium.

I claim:

1. An apparatus for administration of at least two gases to a patient, said apparatus comprising a patient circuit (40) which consists of a circle system for rebreathing and a drive circuit (20), and which is provided with delivery means (45, 46) for supplying fresh gas, and a carbon dioxide absorber (44), said apparatus further comprising an actual value transducer (47) for the gas concentration of one gas type, a desired value transducer (81) for indicating the desired gas concentration, and a control device (80) for maintaining said gas concentration, characterised in that said patient circuit and said drive circuit communicate with each other via an exchanger (30) for open separation, and that said control device (80) comprises a calculating means for determining the gas volume and gas type to be supplied to said patient circuit (40) so as to obtain the desired value concentration.

2. The apparatus as claimed in claim 1, characterised in that the gas volume is determined in such manner that the desired value concentration is obtained by a minimum supply of fresh gas.

3. The apparatus as claimed in claim 1 or 2, characterised in that the gas volume is supplied by pulses to said patient circuit (40).

4. The apparatus as claimed in claim 3, characterised in that the gas pulses are supplied to said patient circuit (40) at large intervals, for example one minute.

5. The apparatus as claimed in any one of claims 1 or 2, characterised in that fresh gas is supplied at different times for different gas types.

6. The apparatus as claimed in any one of claims 1 or 2, characterised in that a computer is included in said control device for calculating and/or checking the supply of gas and/or concentration of gas in said patient circuit.

7. The apparatus as claimed in claims 1 or 2, characterised in that one gas type is xenon.

8. The apparatus as claimed in claims 1 or 2, characterised in that said exchanger (30) comprises a tubular container.

9. The apparatus as claimed in claim 5, characterised in that said container comprises a plurality of tubes connected in series or in parallel.

10. The apparatus as claimed in claim 8, characterised in that said container is filled with corrugated, folded, and/or laminated material.

11. The apparatus as claimed in claim 8 characterised in that said container is internally provided with a mesh.

12. The apparatus as claimed in claim 1, characterised in that said calculating means determines the gas volume and gas type based on the difference between the desired value and actual value concentration of the gas type.

13. The apparatus as claimed in claim 1, characterised in that said calculating means determines the gas volume to be supplied in proportion to a logarithmic function for the quota between the desired value and actual value concentration of the gas type.

14. The apparatus as claimed in claim 12 or 13, characterised in that said calculating means determines the volume to be supplied as the absolute value ln (desired gas concentration/present gas concentration)×(mixing volume)×(regulator amplification).

15. The apparatus as claimed in claim 14, characterised in that said calculating means sets up a test value for the mixing volume and adjusts said value by changing the factor for the regulator amplification in response to the measured gas concentration after the calculated volume has been added.

16. The apparatus as claimed in any one of claims 12 or 13, characterised in that sasid calculating means comprises a microprocessor (80).

17. The apparatus as claimed in claims 1 or 2 or 12 or 13, characterised in that expiration gas passing the drive circuit side of said exchanger (30) during expiration, is delivered back to the drive circuit via a return flow conduit (50).

18. The apparatus as claimed in claims 1 or 2 or 12 or 13, characterised in that said conduit comprises a compressor (54) for compressing the expiration gas.

19. The apparatus as claimed in claims 1 or 2 or 12 or 13, characterised in that said conduit is provided with a gas concentration meter (58) for at least one gas type.

20. The apparatus as claimed in claim 16, characterised in that said conduit (50) is connected to an accumulator bottle (62) adapted to receive gas when the gas concentration passes a predetermined level.

21. The apparatus as claimed in claims 1 or 2 or 12 or 13 characterised in that said drive circuit (30) is provided with an oxygen conduit (21) for filling the drive circuit with oxygen, said oxygen conduit being activated if required.

22. The apparatus as claimed in claim 14 characterised in that said conduit (50) comprises a buffer (56) to equalize volume variations.

23. The apparatus as claimed in any one of claims 1 or 2 or 12 or 13, one gas type administered to the patient being an anaesthetic gas, characterised in that expiration gas which during expiration passes the drive circuit side of the exchanger, is supplied through a recovery conduit (70) to an absorber (75) for anaesthetic gas.

24. The apparatus as claimed in claim 23, characterised in that the anaesthetic gas is xenon, and that said absorber contains a zeolite (76).

25. The apparatus as claimed in claim 24, characterised in that the pressure and temperature in said absorber is set to optimise the absorption of xenon.

26. The apparatus as claimed in claim 23 characterised in that said absorber consists of at least two units through which the gas can be supplied alternatively.

27. The apparatus as claimed in claim 9 characterised in that the tubes are filled with corrugated, folded, and/or laminated material.

28. The apparatus as claimed in claim 9 characterised in that said tubes are internally provided with a mesh.

29. The apparatus as claimed in claim 24, characterised in that said absorber consists of at least two units through which the gas can be supplied alternately.

30. The apparatus as claimed in claim 25, characterised in that said absorber consists of at least two units through which the gas can be supplied alternately.

* * * * *